United States Patent [19]
Christian et al.

[11] Patent Number: 5,163,445
[45] Date of Patent: Nov. 17, 1992

[54] APPARATUS, SYSTEM AND METHOD FOR MEASURING SPATIAL AVERAGE VELOCITY AND/OR VOLUMETRIC FLOW OF BLOOD IN A VESSEL AND SCREW JOINT FOR USE THEREWITH

[75] Inventors: Jeffrey J. Christian, San Jose; Paul D. Corl; Jerome Segal, both of Palo Alto; Ronald G. Williams, Menlo Park, all of Calif.; Wayne C. Haase, Acton, Mass.

[73] Assignee: Cardiometrics, Inc., Mountain View, Calif.

[21] Appl. No.: 759,413

[22] Filed: Sep. 13, 1991

Related U.S. Application Data

[60] Division of Ser. No. 411,339, Sep. 22, 1989, Pat. No. 5,105,818, which is a continuation-in-part of Ser. No. 297,111, Jan. 13, 1989, Pat. No. 4,967,753, which is a continuation-in-part of Ser. No. 36,796, Apr. 10, 1987, abandoned.

[51] Int. Cl.⁵ .............................................. A61N 1/04
[52] U.S. Cl. ................................. 128/785; 604/171; 248/623; 248/624; 248/625
[58] Field of Search .............. 128/785, 786, 802, 912, 128/772; 604/170, 171, 166; 248/617, 623, 624, 625; 464/57, 182

[56] References Cited

U.S. PATENT DOCUMENTS

| | | | |
|---|---|---|---|
| 1,472,782 | 11/1923 | Barber | 464/57 |
| 2,514,394 | 7/1950 | Irving | 464/182 |
| 4,282,885 | 8/1981 | Bisping | 128/785 |
| 4,481,953 | 11/1984 | Gold et al. | 128/786 |
| 4,554,929 | 11/1985 | Samson et al. | 128/772 |
| 4,711,027 | 12/1987 | Harris | 128/785 |
| 4,757,827 | 7/1988 | Buchbinder et al. | 604/170 |

*Primary Examiner*—Francis Jaworski
*Assistant Examiner*—George Manuel
*Attorney, Agent, or Firm*—Flehr, Hohbach, Test, Albritton & Herbert

[57] ABSTRACT

System for measuring a characteristic of flow of liquid in a vessel of a patient comprising a transducer positioned in a vessel in a patient for supplying ultrasonic energy. The transducer produces a substantially uniform beam which encompasses the vessel. The transducer receives ultrasonic energy back scattered from the red blood cells and provides an electrical output signal. A first moment detector is provided which receives the electrical output from the transducer and provides a first moment signal. Normalization is provided to the output of the first moment detector to provide an electrical output representing a characteristic of the flow of the liquid in the vessel.

10 Claims, 7 Drawing Sheets

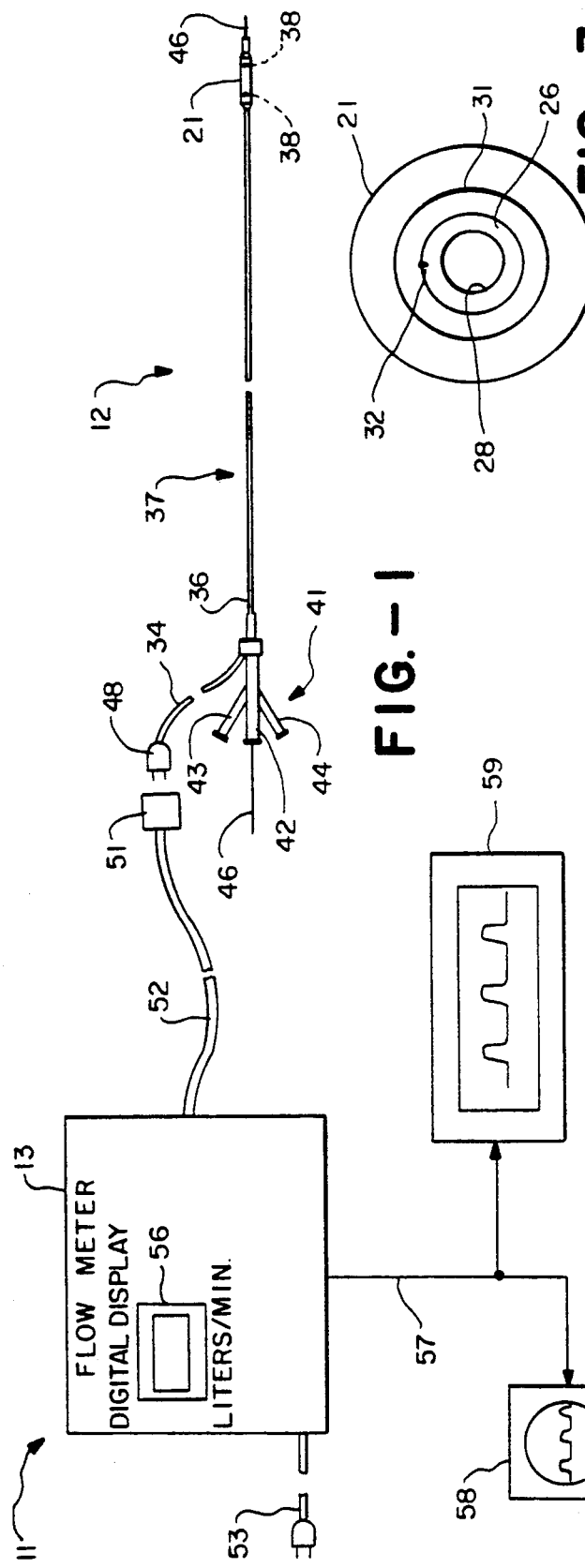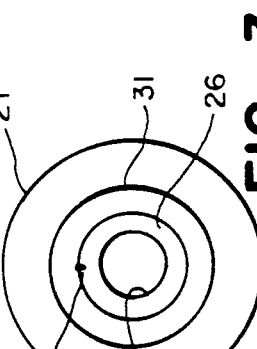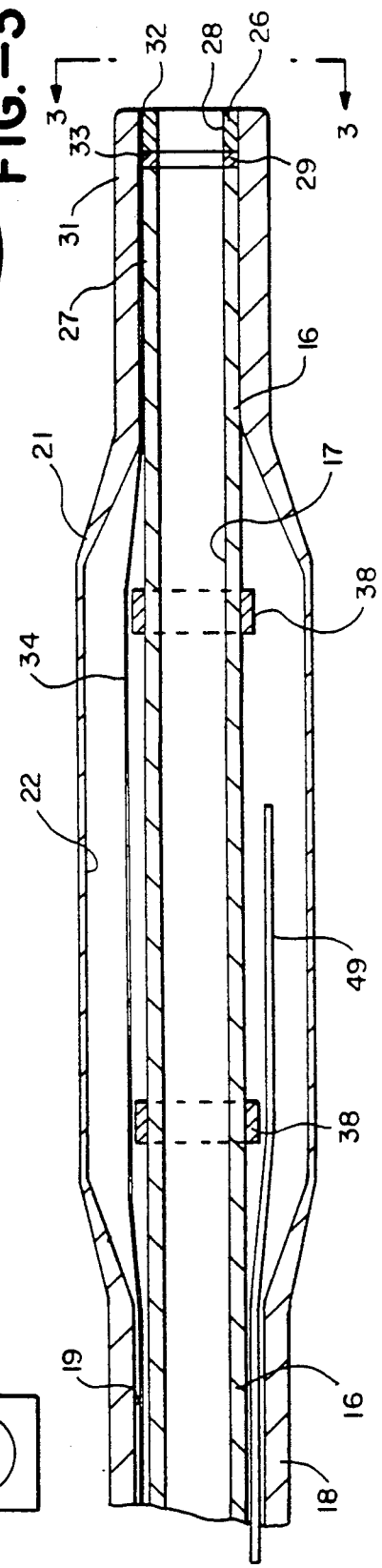

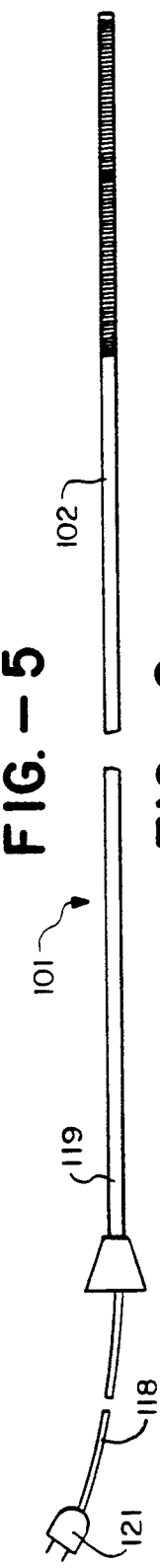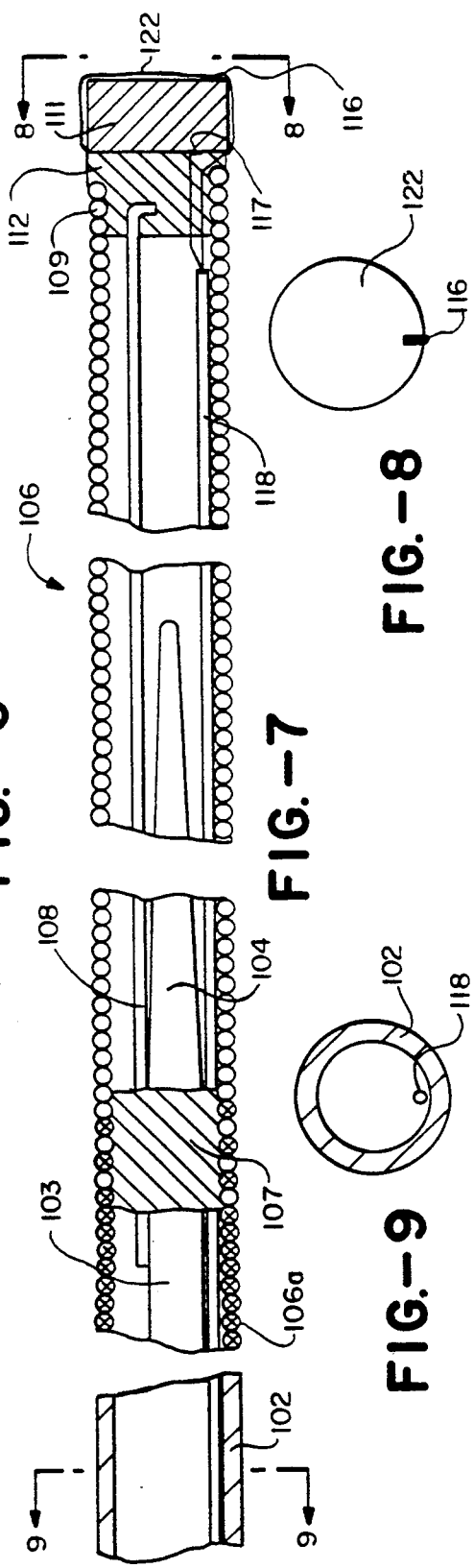

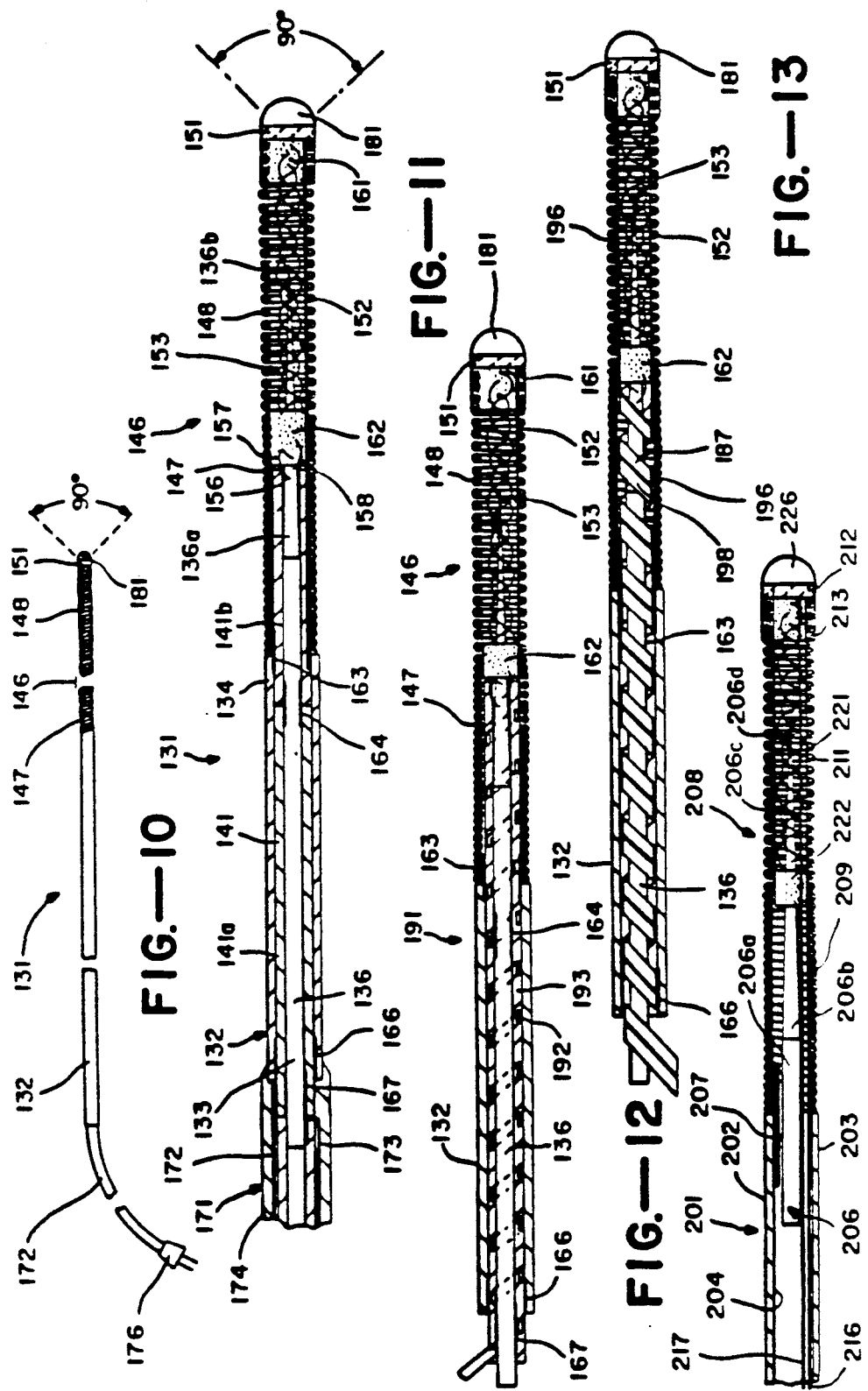

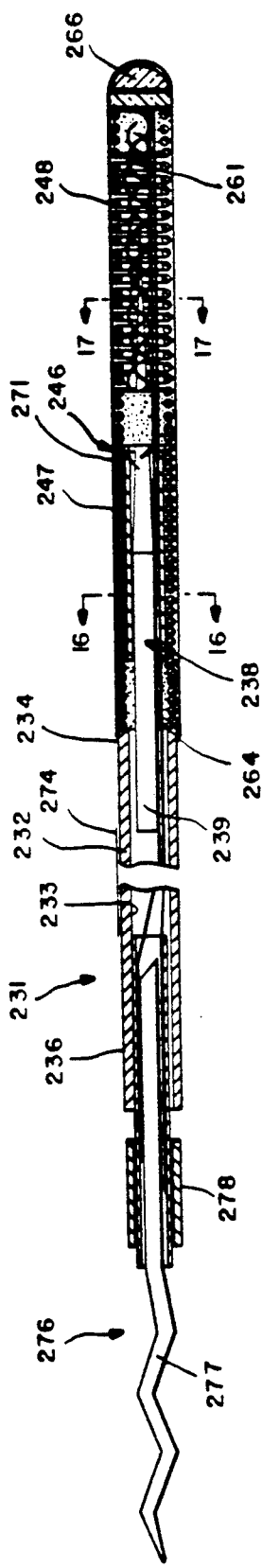
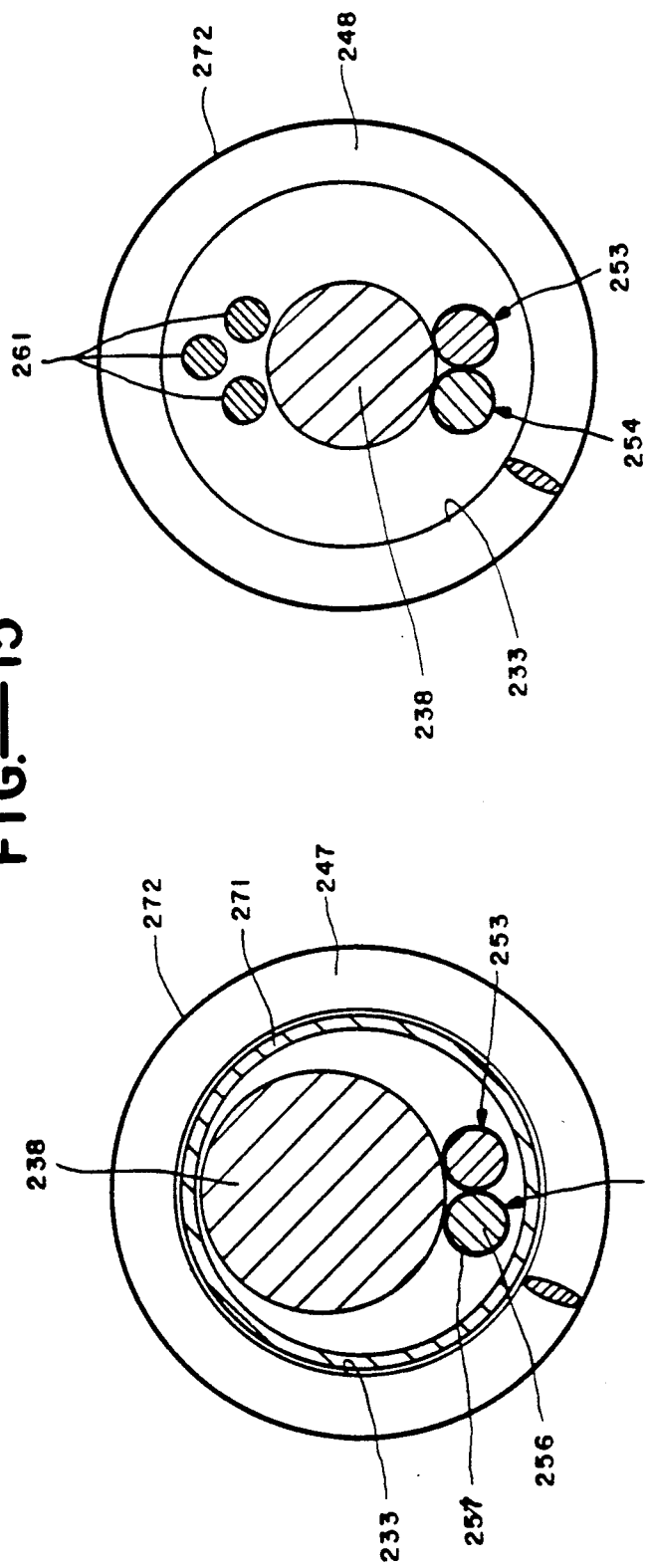
FIG.—15
FIG.—17
FIG.—16

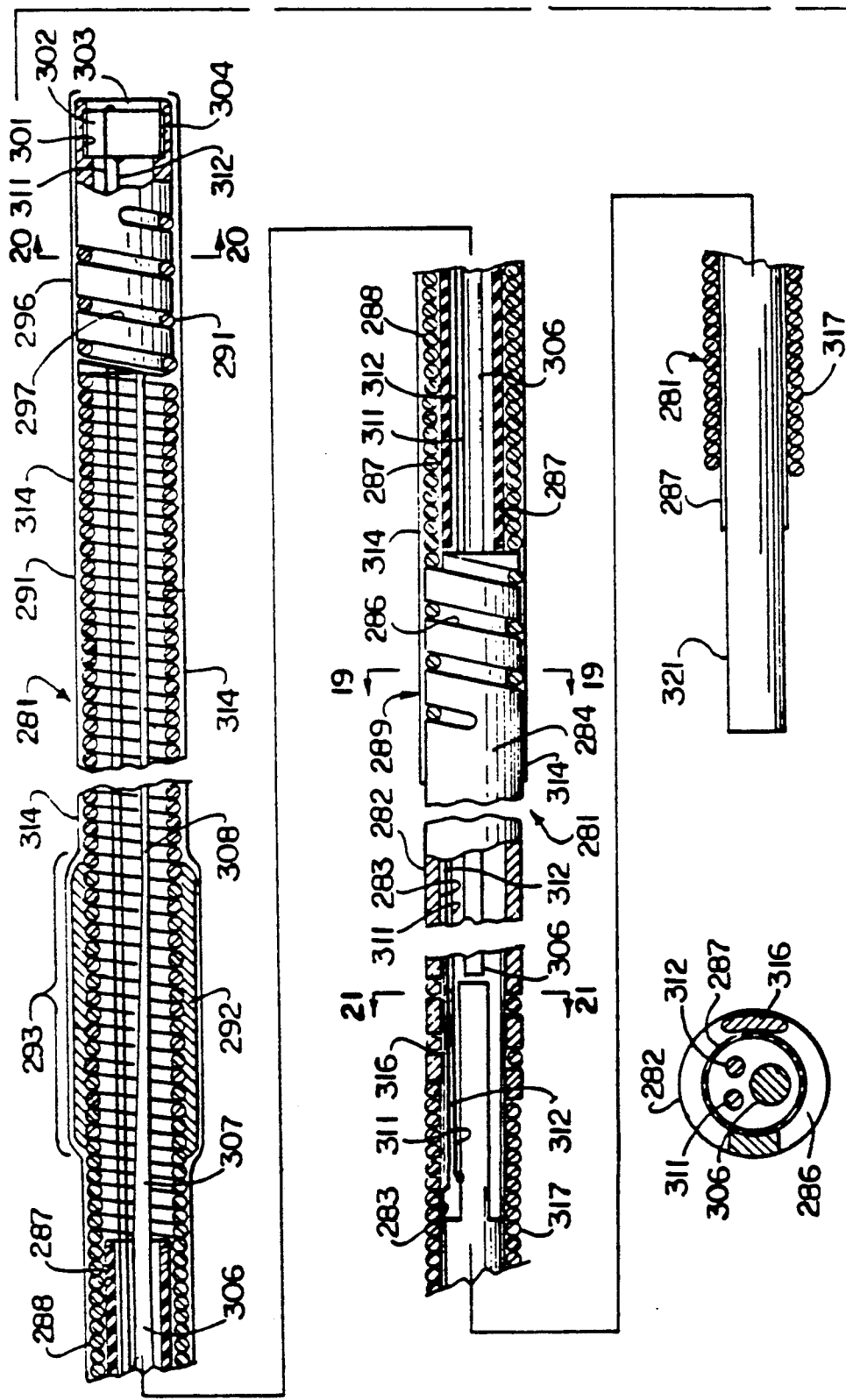

APPARATUS, SYSTEM AND METHOD FOR MEASURING SPATIAL AVERAGE VELOCITY AND/OR VOLUMETRIC FLOW OF BLOOD IN A VESSEL AND SCREW JOINT FOR USE THEREWITH

This is a division of application Ser. No. 07/411,339 filed Sep. 22, 1989 now U.S. Pat. No. 5,105,818, which is a continuation-in-part of application Ser. No. 297,111 filed on Jan. 13, 1989 now U.S. Pat. No. 4,967,753 which is a continuation-in-part of application Ser. No. 036,796 filed on Apr. 10, 1987 now abandoned.

This invention relates generally to an apparatus, system and method for measuring spatial average velocity and/or volumetric flow of blood in a vessel and more particularly, to such an apparatus, system and method using ultrasonics and a screen joint for use therewith.

Diagnostic catheters have heretofore been provided for measuring intravascular pressure and blood flow using thermal dilution, dye dilution and oxygen consumption methods. More recently, intravascular catheters have been developed which measure instantaneous flow velocity utilizing ultrasonic Doppler transducers to measure the "Doppler shift" created by movement of red blood cells, acting as targets, within the blood vessel or organ to which a measurement is being made. Doppler systems of that character have been described extensively in the literature, as for example, in Cole in al "Pulsed Doppler Coronary Artery Catheter", *Circulation*, Vol. 56, No. 1, July 1977 and Sibley et al., "Subselective Measurement of Coronary Blood Flow Velocity Using A Steerable Doppler Catheter" *Journal of American College of Cardiology* (Vol. 8, No. 6 December 1986 1332-40). Typically the Doppler catheters utilized in such systems are useful only for the measurement of flow velocity within a small sample volume contained within the blood vessel of interest. Volumetric flow cannot be accurately determined utilizing such Doppler systems. Additional information such as vessel dimensions, flow profile and incidence angle between the ultrasound beam and flow must be known in order to accurately determine volumetric flow. Cutaneous Doppler systems have been developed which allow volumetric flow measurements to be performed and which are independent of Doppler angle, vessel size and velocity profile. These cutaneous Doppler systems utilize a uniform insonification method as taught by Hottinger and Meindl and described in "Blood Flow Measurement Using Attenuation-Compensated Volume Flowmeter" *Ultrasonic Imaging*, Vol. 1, No. 1, 1979 and U.S. Pat. Nos. 4,007,236, 3,888,238, 4,431,936 and 4,519,260. Volumetric flow measurements made with such a method require the use of two coplanar ultrasonic beams which are precisely positioned within the vessel of interest. Typically, a large uniform beam in the near field of a relatively large, cutaneous acoustic transducer is used to insonify the entire dimension in the blood vessel of interest. A second coplanar reference beam is contained entirely within the blood vessel of interest is used to generate a scale factor for conversion of flow related parameters into a quantitative measurement of true flow. Problems have been encountered with such a method because of the difficulty of placing the two required ultrasonic beams in the desired precise locations with respect to the vessel. It is difficult to assure that the large uniform beam encompasses the entire blood vessel and that the reference beam is totally contained within the blood vessel. In addition it has been found that neighboring vessel, if contained within the measurement sample volume, will cause inaccuracies in flow measurement. Furthermore, additional errors may result because of different tissue attenuation characteristics encountered in the two ultrasonic paths. There is therefore a need for a new and improved apparatus, system and method for measuring volumetric flow of blood in a vessel which overcomes these difficulties.

In general, it is an object of the present invention to provide an apparatus, system and method for measuring spatial average velocity and/or volumetric flow of blood in a vessel.

Another object of the invention is to provide an apparatus, system and method of the above character in which uniform insonification is provided in the vessel in the far field of an acoustic transducer, such uniform beam completely covering the entire lumen of the vessel of interest.

Another object of the invention is to provide an apparatus, system and method of the above character which avoids interference from neighboring blood vessels.

Another object of the invention is to provide an apparatus, system and method of the above character which places a single transducer entirely within a blood vessel of interest in order to provide a single uniform beam which insonifies the entire vessel lumen and provides a signal for measurement of volumetric flow.

Another object of the invention is to provide an apparatus, system and method of the above character which utilizes a single transducer which is placed entirely within the blood vessel of interest and supplies a signal to a first moment detector via pulsed Doppler circuitry.

Another object of the invention is to provide an apparatus, system and method in which the first moment detector weights the various Doppler shift frequency components in accordance with the number of red blood cells (acoustic scatters) traveling at velocities normal to the plane of the sample volume of the ultrasonic beam in the blood vessel.

Another object of the invention is to provide an apparatus, system and method of the above character in which the first moment signal is divided by the Doppler power signal to obtain a measurement which is representative of the spatial average velocity of the flow of blood in the vessel.

Another object of the invention is to provide an apparatus, system and method of the above character in which a calculated correctional factor is applied to the first moment signal obtained from the transducer via the pulsed Doppler circuitry to obtain a measurement which is representative of the volume of blood flow within the vessel.

Another object of the invention is to provide an apparatus, system and method of the above character in which intravascular blood flow measurements are made using pulsed Doppler circuitry, with little or no interference from other blood vessel beyond the boundaries of the walls of the vessel of interest.

Another object of the invention is to provide an apparatus, system and method of the above character in which extremely small transducers are provided at the distal extremities of the flexible elongate element disposed within the vessel of interest.

Another object of the invention is to provide an apparatus in which the flexible elongate element is a guide wire.

Another object of the invention is to provide an apparatus, system and method in which intravascular Doppler volumetric flow measurements are independent of angle and orientation of the transducer.

Another object of the invention is to provide an apparatus of the above character in which the flexible elongate element utilizes a concentric construction.

Another object of the invention is to provide an apparatus of the above character in which the flexible elongate element has excellent torsional and mechanical properties.

Another object of the invention is to provide an apparatus of the above character in which the flexible elongate element has desirable electrical properties.

Another object of the invention is to provide an apparatus of the above character in which shielding is provided in the flexible elongate element to minimize electrical noise.

Another object of the invention is to provide an apparatus of the above character in which a coaxial construction is utilized for the flexible elongate element.

Another object of the invention is to provide an apparatus of the above character in which a lens is provided for the transducer to provide a uniform beam over a predetermined angle.

Another object of the invention is to provide an apparatus, system and method of the above character which is particularly suitable for use in angioplasty.

Another object of the invention is to provide an apparatus, system and method of the above character which is relatively immune to the effects of electrical fields so that the sensitivity remains substantially unchanged over time.

Another object of the invention is to provide an apparatus of the above character in which the guide wire is provided with a protective covering so that blood or other saline solutions in the vessel cannot come in contact with the electrical leads utilized.

Another object of the invention is to provide a guide wire of the above character in which conformal protective coatings are utilized.

Another object of the invention is to provide a guide wire of the above character in which an additional protective sheath is utilized while still providing the desired amount of stiffness at the distal extremity of the guide wire without unduly affecting the floppy characteristics.

Another object of the invention is to provide a guide wire of the above character which is provided with a screw joint for securing the transducer.

Additional objects and features of the present invention will appear from the following description in which the preferred embodiments are set forth in detail in conjunction with the accompanying drawings.

FIG. 1 is a schematic illustration of a system and apparatus for measuring volumetric flow of blood in a vessel incorporating the present invention.

FIG. 2 is an enlarged distal extremity of the flexible elongate element in the form of a balloon dilatation catheter shown in FIG. 1.

FIG. 3 is an end elevational view of the balloon dilatation catheter shown in FIG. 2 looking along the line 3—3 of FIG. 2.

FIGS. 5A–5E are timing diagrams for the circuitry shown in FIG. 4.

FIG. 6 is a side elevational view of another embodiment of a flexible elongate element in the form of a guide wire.

FIG. 7 is an enlarged cross sectional view of the distal extremity of the guide wire shown in FIG. 6.

FIG. 8 is a view taken along the lines 8—8 of FIG. 7.

FIG. 9 is a cross sectional view taken along the line 9—9 of FIG. 7.

FIG. 10 is a side elevational view of another embodiment of a flexible elongate element incorporating the present invention in the form of a guide wire having a coaxial construction.

FIG. 11 is a cross-sectional view of the distal extremity of the guide wire shown in FIG. 10.

FIG. 12 is a cross-sectional view of the distal extremity of another guide wire incorporating the present invention which is particularly useful when electrical noise problems are encountered.

FIG. 13 is a cross-sectional view similar to FIG. 12 showing another embodiment of a guide wire incorporating the present invention.

FIG. 14 is a cross-sectional view similar to FIGS. 12 and 13 showing another embodiment of a guide wire incorporating the present invention.

FIG. 15 is a side elevational view of another embodiment of a guide wire incorporating the present invention provided with a protective covering to protect the same from attacks by blood and other saline solutions.

FIG. 16 is an enlarged cross sectional view taken along the lines 16—16 of FIG. 15.

FIG. 17 is an enlarged cross sectional view taken along the lines 17—17 of FIG. 15.

FIG. 18 is a partial view partially in cross section of another embodiment of a guide wire incorporating the present invention utilizing screw joints.

FIG. 19 is a cross sectional view taken along the line 19—19 of FIG. 18.

Figure 4:
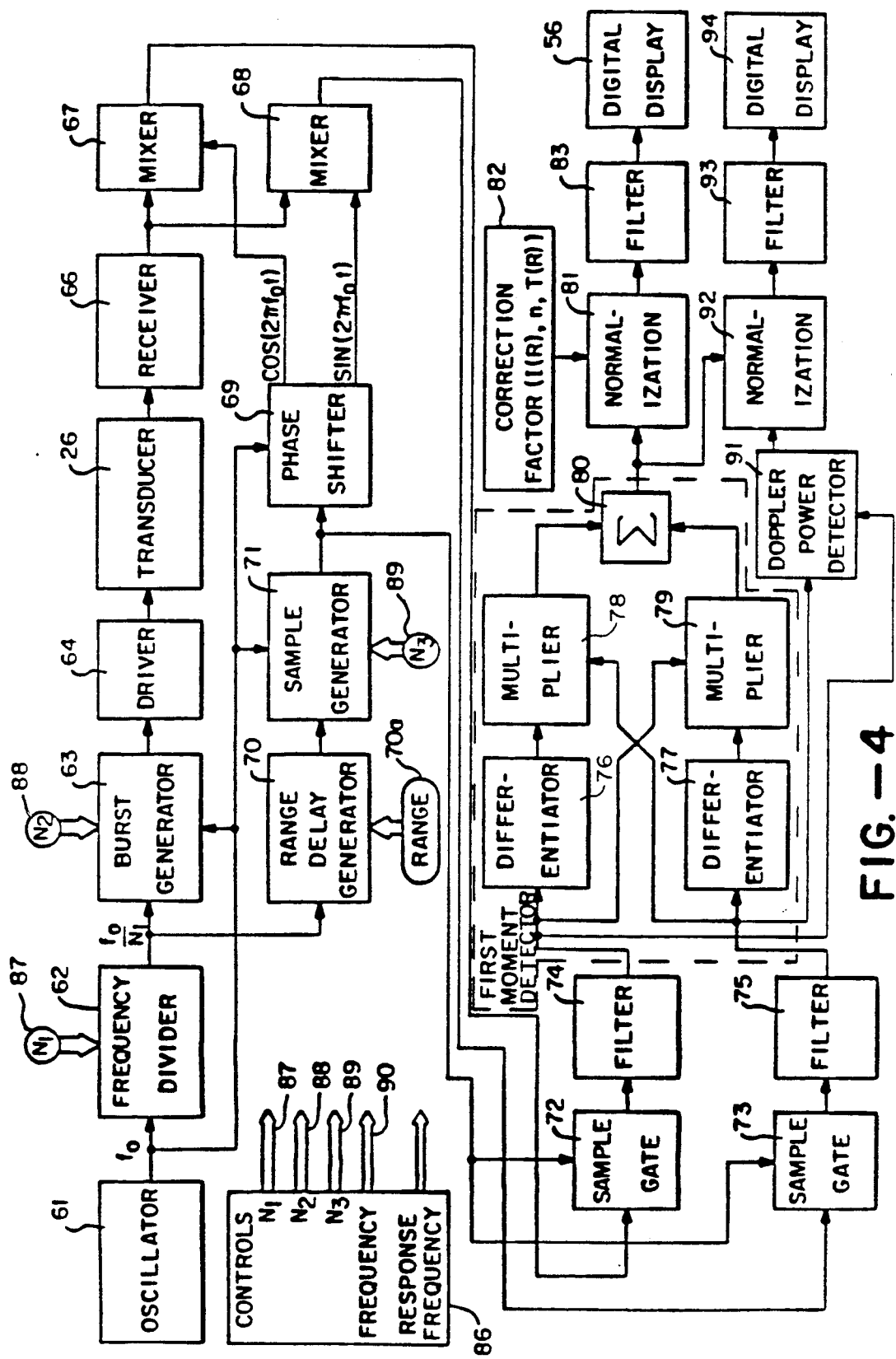
FIG. 4 is a block diagram of the electronic circuitry utilized in the system and apparatus shown in FIG. 1.

The system and method for measuring volumetric blood flow in a vessel of a patient is comprised of a transducer which is disposed within the vessel. Means is provided for supplying radio frequency energy to the transducer to cause the transducer to create a beam of ultrasonic energy which encompasses the vessel. Ultrasonic energy reflected by the red blood cells in the vessel is received by the transducer and the Doppler shift frequency is converted to an electrical signal which is supplied to a first moment detector via pulsed Doppler circuitry. A Doppler power detector is utilized to normalize the output from the first moment detector to provide the spatial average velocity of the flow of blood in the vessel. In addition or alternatively, a calculated correctional factor is applied to normalize the output from the first moment detector to provide the volumetric flow of blood through the vessel.

More in particular, the system 11 for measuring volumetric flow of blood in a vessel consists of a flexible elongate transducer carrying device 12 which is connected to a flow meter 13. The flexible elongate transducer carrying device 12 as shown in FIG. 1 is in the form of a balloon dilatation catheter. The catheter can be constructed in the manner disclosed in U.S. Pat. No. 4,323,071. Thus it is provided with an inner flexible tubular member 16 having a lumen 17 extending therethrough. It also consists of an outer flexible tubular member 18 which is disposed coaxially on the inner flexible tubular member 16 and forms an annular flow passage or lumen 19. A balloon 21 is carried by the distal extremity of the outer member 18 and as shown can be formed integral therewith. The lumen 19 opens into the interior 22 of the balloon and is used for inflating and deflating the balloon 21. The inner member 16 and the outer member 18 can be formed of suitable plastic such as polyethylene. It should be appreciated that if desired, rather than the co-axial construction hereinbefore described for the catheter, a single plastic flexible elongate tubular member can be provided having first and second lumens formed therein in which one serves as a guide wire lumen and the other serves as a balloon inflation lumen. In addition, it should be appreciated that if desired, a separate balloon can be provided rather than an integral balloon in which the separate balloon is bonded to the outer flexible tubular member 18.

A transducer 26 is carried by the distal extremity 27 of the inner flexible tubular member 16. The transducer 26 can be constructed of an appropriate piezoelectric material such as lead-titanate-zirconate ceramic. For reasons hereinafter described, the transducer is in the form of a toroid which has a central opening 28 that is in registration with the lumen 17. The transducer 26 is secured to the distal extremity 27 of the inner member 16 by a suitable adhesive such as a tungsten-oxide loaded epoxy backing material 29. The distal extremities 27 and 31 can be sealed with respect to each other in a suitable manner such as by heat shrinking the distal extremity 31 of the outer tubular member 18 onto the distal extremity 27 of the inner tubular member 16. Alternatively if desired, a suitable adhesive can be provided and wicked between the distal extremities 27 and 31 so that a liquid-tight seal is formed between the distal extremities of the members 16 and 18.

As can be seen from FIG. 2, the transducer 26 is also supported by the outer distal extremity 31 of the outer flexible tubular member 18. Front and rear electrical connections 32 and 33 are provided on the transducer 26 and are connected to a two conductor wire 34 which extends rearwardly away from the distal extremity. The two conductor wire 34 is disposed between the outer tubular member 18 and the inner tubular member 16 and extends rearwardly through the balloon 21 and through the lumen 19 to the proximal extremity 36 of the catheter 12.

A pair of radiopaque markers 38 which are spaced apart within the balloon are carried by the inner tubular member 16 to facilitate visualizing of the balloon during use of the same. The markers 38 can be formed of a suitable material such as gold bands, or alternatively, as coils of platinum wire.

The inner tubular member 16 and the outer tubular member 18 as well as the toroidal transducer 26 can have suitable dimensions. For example, the lumen 17 in the inner tubular member can have a suitable dimension such as 0.021 inches as can the opening 28 in the toroidal transducer 26. The tubular member 16 can have an outer diameter of 0.031 inches whereas the outer tubular member 18 can have an outside diameter of 0.048 inches.

A three-arm adapter 41 of a conventional type is mounted on the proximal extremity 36 of a shaft 37 which is formed by the inner tubular member 16 and the outer tubular member 18. The tubular members 16 and 18 can have a suitable length as, for example, approximately 175 centimeters.

The three-arm adapter 41 is provided with a central arm 42 and side arms 43 and 44. The central arm 42 is in communication with the lumen 17 and the inner tubular member 16 is adapted to receive a guide wire 46 of a conventional construction which is utilized for facilitating placement of the catheter as hereinafter described. The side arm 43 can be utilized as an inflation and deflation port and is in communication with the annular flow passage 19 that is in communication with the interior 22 of the balloon 21. The two conductor wire 34 can be brought out from the lumen 19 just distal of the three-arm adapter 41 as shown in FIG. 1 and is connected to a male connector 48. The side arm 44 is also in communication with the lumen 19 an is adapted to receive a vent tube 49 of a conventional type which extends into the interior 22 of the balloon and is utilized for venting air from the balloon as the balloon is inflated.

The male connector 48 is adapted to be connected to a female connector 51 provided on cable 52 which is connected to the flow meter 13. The flow meter 13 is provided with a power cord which is adapted to be connected to a suitable source of 60 cycle 110 volts AC. The flow meter 13 is provided with a digital display 56 which gives it readout in liters per minute. The flow meter 13 is also provided with an analog output which can be utilized in conjunction with an oscilloscope 58 and/or a strip chart recorder 59.

The flow meter 13 includes the electronics which is shown in block diagram in FIG. 4. As shown therein, the electronics consists of a plurality of blocks 61 through 94 which serve functions as hereinafter described. The apparatus also includes a control panel or computer 86 which provides control outputs 87 through 90 which are used in a manner hereinafter described.

Operation and use of the system and apparatus in performing the method of the present invention may now be briefly described as follows. Let it be assumed that the system and apparatus is to be utilized in conjunction with a balloon angioplasty procedure. In such a procedure, the balloon 21 is first inflated outside the body with a radiographic contrast liquid through the side arm 43. Air within the balloon is forced out through the balloon vent tube 49. After the balloon 21 has been completely inflated so there are no air bubbles in the same, the balloon is deflated. The guide wire 46 is inserted through the central arm 42 until it extends beyond the distal extremity of the catheter 12. The catheter 12 with the guide wire 46 therein can then be advanced into the blood vessel of the patient in a conventional manner so that the balloon is in the vicinity of the stenosis to be dilated. It then may be desirable to ascertain the volume blood flow through the stenosis prior to dilation. To accomplish this, the male connector 48 is connected into the female connector 51 and the flowmeter 13 is placed in operation.

In the making of volumetric flow measurements with flowmeter 13, utilizing a single beam, it is necessary that there be provided a relatively uniform beam which extends over the entire cross sectional area of the vessel being examined which can range in size form 1 millimeter to 35 millimeters. Assuming that the vessel in which the catheter 12 is positioned has a diameter of approximately 2.5 millimeters, a crystal or transducer 26 is utilized having a frequency of 6.7 MHz and an outer diameter of approximately 0.75 millimeters. A beam is produced with a divergence angle of approximately 20°. This divergence angle can be calculated approximately as follows:

$$\text{Divergence angle} = \frac{\lambda}{D}$$

$$\text{where } \lambda = \frac{c}{f}$$

where c = the velocity of sound which is approximately 1.54 millimeters per microsecond
where D is the diameter of the transducer crystal in millimeters, and where f is the frequency of the crystal in megahertz Using these formulas, the calculations can be made as follows:

$$\lambda = \frac{1.56}{6.7} = .25 \text{ mm}.$$

$$\text{divergence angle} = \frac{.25}{.75} = \frac{1}{3} \text{ of a radian} = 20°$$

Thus it can be seen with a transducer of that size and that frequency, a beam is produced which has a divergence angle greater than at least 10° as for example, from approximately 10° to 120°. At a divergence angle of approximately 20° with a range gate depth ranging from 1 to 40 millimeters and preferably at approximately 10 millimeters which is in the far field, flowmeter 13 in conjunction with transducer 26 will produce a relatively uniform beam over the cross-sectional area of a vessel having a diameter of approximately 2.5 millimeters. An ultrasonic beam of this dimension would thus encompass the entire lumen of an average coronary artery.

The oscillator 61 generates the desired frequency $f_o$ which with the present transducer is 6.7 MHz. This signal from the oscillator 61 is supplied to the frequency divider 62 which generates a signal at a frequency $f_o/N1$ where N1 represents the division provide by the frequency divider 62. N1 is determined by the output 87 from the computer 86. The outputs from the oscillator 61 and from the frequency divider 62 are both supplied to a burst generator 63 to provide a signal output which is comprised of N2 consecutive cycles at frequency $f_o$ and repeating every N1 cycles of the frequency $f_o$. The number N2 is supplied from the computer output 88.

The output from the burst generator 63 is supplied to the driver 64 which amplifies the signal and has an appropriate output impedance to drive the transducer 26 hereinbefore described. The transducer 26 converts the electrical drive signal from the driver 64 into an acoustic wave which travels through the blood within the vessel of interest. The output of the frequency divider 62 thus determines the repetition rate of the system, that is the rate at which acoustic-wave packets are emitted from the transducer 26. As the acoustic wave travels through the blood the red cells in the blood back-scatter acoustic energy and generate a Doppler shifted signal which returns to the transducer 26. The returned acoustic energy is converted back into electrical energy by the transducer 26. This electrical signal from the transducer 26 is then amplified by the receiver 66 and is supplied to mixers 67 and 68.

The output $f_o$ from the oscillator is also supplied to a phase shifter 69 which generates two output signals which are sine and cosine waves that have a 90 degree phase shift between them. The cosine output from the phase shifter 69 is supplied to the mixer 67 whereas the sine output from the phase shifter 69 is supplied to the mixer 68. The use of two such signals which are 90 degrees shifted in phase provides a system which is quadrature based and makes it possible to distinguish between forward and reverse flow.

It should be appreciated that, if desired, other signal processing techniques well-known to those skilled in the art can be utilized for obtaining directional flow measurement as, for example, an offset frequency could be utilized. Alternatively separation of forward and reverse flows by single side band phasing techniques can also be employed. It should also be appreciated in those situations where the flow direction is known or for example is known to be unidirectional, simplified electronic circuitry can be utilized. It should also be appreciated that other signal processing techniques, such as spectral analysis, may be utilized to estimate the moments of the Doppler signal.

The output from the frequency divider 62 is also supplied to a range delay generator 70 which supplies its output to a sample generator 71. The output of the range delay generator 70 is in the form of a pulse which begins at the same time that the burst generator 63 begins the transducer drive burst and which ends at a time determined by the range input 70a to the range delay generator 70 as shown in FIG. 5. The sample generator 71 generates a pulse which begins at the end of the range delay generator output pulse and which has a pulse width equal to N3 cycles of frequency $f_o$. The relationship between the output signals from the oscillator 61, the frequency divider 62, the burst generator 63, the range delay generator 70 and the sample generator 71 are illustrated in the timing diagram shown in FIG. 5. In general N2 and N3 are made equal for optimum signal-to-noise performance, although they are shown as separate values in FIGS. 4 and 5.

The mixers 67 and 68 generate output signals that are a product of their respective input signals. The output signals from the mixer 67 and 68 are supplied to sample gates 72 and 73. The sample gate 72 may be a "sample and hold" circuit which generates an output which follows the input from the mixer 68 during the pulse time from sample generator 71 and which holds the last value from the time the pulse ends until the next pulse. Alternatively the gate 72 can be a "gate, integrate and hold" circuit which generates an output proportional to the time integral of the output signal from the mixer 68 over the period of the sample pulse from sample generator 71. The principal difference between such two forms of the gate 12 relates to the particular shape of the sample volume inside the blood vessel through which the volume flow is measured. The sample gate 73 is identical to the sample gate 72 and performs an equivalent operation on the output signal from the mixer 67.

The outputs from the sample gates 72 and 73 are fed into filters 74 and 75 respectively. The filters 74 and 75 are combinations of low pass and high pass filter sections and are utilized to determine the effective blood velocity ranges over which the volume flow measurements are to be made. The low frequency cutoff of the high pass filter section determines the lowest velocity included in the flow calculation and rejects the signals from slow moving vessel walls. The high frequency cutoff of the low pass filter is generally adjusted to be slightly less than one-half of the system repetition rate, as determined by the frequency divider 62. The filter 73 and 74 may also include compensation for the "(sine x)/(x)" filtering effect of the sample gate 72 and the sample gate 73.

The outputs from the filters 74 and 75 are supplied to differentiators 76 and 77 which supply their outputs to multipliers 78 and 79 with the outputs of the multipliers 78 and 79 being supplied to a summation block 80. The differentiators 76 and 77, the multipliers 78 and 79 and the summation block 80 constitute a "first moment detector" which generates an output proportional to the spectral first moment of the two input signals from the filters 74 and 75. The differentiators 76 and 77 generate output signals proportional to the time derivative of their respective input signals. The multipliers 78 and 79 generate output signals proportional to the product of their respective input signals. The summation block 80 generates an output signal proportional to the difference between the output signal from the multiplier 78 and the output signal from the multiplier 79. The first moment detector hereinbefore described has been known as a "cross-correlation detector". Other first moment detectors such as "square-root-of-frequency" versions can be utilized. The first moment detector which is shown in FIG. 4 has been chosen because of its better signal-to-noise performance. Alternatively, the first moment may be calculated from a spectral analysis of the Doppler shift frequency.

The output of the summation block 80 supplies a first moment signal. The first moment signal which is supplied from the summation block 80 is applied to a normalization block 81 which receives calculated correction factor signal from a block 82. The correction factor which is supplied is hereinafter described.

The output from the normalization block 81 is supplied to a filter 83. The filter 83 determines the final bandwidth of the volume flow output calculation. By way of example for bandwidths in the 1 to 50 hertz range, the flow output follows the instantaneous value of the volumetric blood flow. For lower bandwidths in the 0 to 1 hertz range, the flow output is proportional to the average (mean) volume of blood flow. The volume flow output signal from the filter 83 is supplied to the digital display 56 to provide an output digital display in the form of liters per minute. This same volume flow output signal can be supplied to the oscilloscope 58 and the strip chart 59 if desired.

The mathematical calculations which are performed by the circuitry shown in FIG. 4 are based on the following. The instantaneous volumetric flow or volume flow $\dot{Q}$ (t) of a fluid across a surface, S, is defined as:

$$\dot{Q}(t) = \int_S v(t) \cdot dA \quad (1)$$

where v(t) is the velocity vector of the fluid at any point on surface S, dA is the elemental area vector perpendicular to the surface and the symbol "·" indicates the vector dot-product. The spectral first moment, M1, of the received power is defined as $$M1 = \int f S(f) df \quad (2)$$

where f is frequency and S(f) is the power spectrum of the received Doppler-shifted signal.

The above calculations have been based upon the assumption of a uniform acoustic power density in the ultrasonic beam. It is also assumed that a first-order, independent scattering process takes place, that the acoustic wavelength is much greater than the scattering particle size and that there is a uniform distribution of scatterers throughout the acoustic beam. Using these assumptions the first moment of the power spectrum of the received signal is:

$$M1 = I(R)\eta T(R)\dot{Q} \quad (3)$$

where I(R) is the transducer sensitivity at range R for the ultrasonic beam, $\eta$ is the volumetric scattering coefficient of blood and T(R) is the round trip transmission efficiency representing the effects of attenuation of the acoustic power caused by the blood.

Equation (3) shows that the volume flow of blood can be estimated by first measuring the first moment of the power spectrum of the received Doppler-shifted signal and then correcting the measurement in accordance with the three parameters, I(R), $\eta$ and T(R). Different methods are available for the determination of these parameters. One method is to separately determine the parameters. The first factor, I(R), can be measured in conventional beam pattern test facilities. The second factor, $\eta$, can be measured experimentally and is not expected to deviate from the experiments due to the consistency of the hematocrit level. The third factor, T(R), can also be measured experimentally. Of the three parameters, I(R) and $\eta$ would normally remain constant for a given value of R.

In most flow measurement situations, the value for T(R) would not be well controlled and would introduce significant errors. It is for this reason that a single intravascular probe is utilized in conjunction with a well-controlled intervening medium such as blood between the transducer and the sample volume. Furthermore, since the attenuation in the blood is significantly less than the attenuation in tissue, the effect of the T(R) term is significantly less than for cutaneous flowmeters. In addition since the attenuation in the blood is less than in tissue, the sensitivity of the final estimate of blood flow to the actual coefficient of attenuation is significantly less. Additionally, since the attenuation in blood is significantly less than attenuation in tissue, any signals from other vessels outside the vessel of interest will be so strongly attenuated as to become insignificant.

Another method for determining the three above-identified parameters is to combine all three in a single calibration. This can be accomplished by comparing Doppler determined flow with the actual flow output, measured for example by collecting the flow volume in a measuring device, and thus determining the calibration relationship between M1 and Q.

From the foregoing it can be seen that relatively accurate measurement of volumetric blood flow can be obtained in a vessel without the use of a second transducer or a second ultrasonic beam. Additionally, accurate volumetric flow measurements can be made utilizing a single transducer which are independent of the angle and position of the transducer in the vessel. By selecting the appropriate frequencies and the appropriate size for the transducer it is possible to obtain a beam divergence angle of greater than 10°, as for example, a range from 15° to 120° in order to ensure that at a selected range depth in the far field region a relatively uniform beam will be produced over the entire cross-sectional area of the vessel. By utilizing previously calculated scale factors in the correction factor block 82, the first moment of flow can be utilized to calculate instantaneous volumetric flow through the vessel before the balloon dilation procedure. As soon as this measurement has been made, the balloon can be advanced into the stenosis and inflated to enlarge the stenosis. After this has been accomplished, the balloon 21 can be withdrawn proximal to the stenosis. Another flow measurement can thereafter be made to ascertain the volumetric blood flow after the dilation procedure. If the volumetric blood flow is inadequate, the balloon can be again advanced into the stenosis and another dilation can be performed. Alternatively, if a larger balloon size is desired, an exchange wire can be substituted for the guide wire 46 and a dilatation catheter having a larger diameter balloon can be utilized to cause a greater enlargement of the stenosis in the vessel. Thereafter, another volumetric flow measurement can be made.

In addition to, or alternative to, the volumetric flow measurement hereinbefore described, the spatial average velocity of blood flow in the vessel can be measured as shown in FIG. 4 by taking the outputs from the filters 74 and 75 and supplying the same to a Doppler power detector 91. The Doppler power detector 91 generates an output signal which is proportional to the power contained in the two input signals from the filters 74 and 75. The output from the Doppler power detector 91 as well as the first moment signal output from the summation block 80 are supplied to the normalization block 92 wherein the first moment signal is divided by the Doppler power signal. The output from the normalization block 92 supplies a signal which is proportional to the spatial average velocity of blood flow in the vessel. The output from the normalization block 92 is supplied to a filter 93 which determines the final bandwidth of the spatial average velocity calculation. By way of example for bandwidths in the range of 1 to 50 hertz, the spatial average velocity output follows the instantaneous value of the spatial average velocity of blood flow within the vessel. For lower bandwidths in the 0 to 1 hertz range, the spatial average velocity output is proportional to the time average (mean) of the spatial average velocity within the vessel. The spatial average velocity output signal from the filter 93 is supplied to a digital display 94 to provide an output display in centimeters per second. This same spatial average velocity output signal is supplied to the oscilloscope 58 and the strip chart recorder 59 if desired.

The spatial average velocity, $<v(t)>$, is defined as:

$$<v(t)> = \frac{\dot{Q}(t)}{A(t)} \tag{4}$$

where $\dot{Q}(t)$ is the volumetric flow as previously defined, and $A(t)$ is the cross-sectional area of the vessel. The zeroth moment, M0, of the power spectrum is defined as:

$$M0 = \int S(f)df \tag{5}$$

where f is frequency and S(f) is the power spectrum of the received Doppler-shifted signal. The zeroth moment is equal to the power contained in the Doppler signal.

The following derivation is based on the previously discussed assumptions of a uniform ultrasonic beam, first-order independent scattering and small scatterer size. It is further assumed that the echoes from non-blood scatterers (e.g. vessel walls and surrounding tissue) are eliminated with high-pass filtering based on the presumption that these extraneous tissues will be moving at lower velocities than the blood cells, and hence they will be represented by lower frequencies in the power spectrum.

Under these assumptions, the first moment of the power spectrum of the received signal is:

$$M1 = I(R)\eta T(R)\dot{Q} \tag{6}$$

where I(R), $\eta$, T(R) and $\vec{Q}$ are the previously described transducer sensitivity, volumetric scattering coefficient, round-trip transmission efficiency and volumetric flow rate. Under the same assumptions, the zeroth moment of the power spectrum of the received signal is:

$$M0 = I(R)\eta T(R)gA \tag{7}$$

where A is the vessel cross-sectional area, and g is a geometric factor relating the vessel cross-sectional area to the portion of the doppler sample volume which lies within the blood stream. In general, g is dependent on the transducer angle, the transducer position, the range of the Doppler sample volume and the vessel size. However, if the range for the sample volume is chosen to be large with respect to the vessel diameter, then the geometric factor, g, will be approximately equal to 1, and substantially independent of transducer position and angle. In this case, the zeroth moment becomes:

$$M0 I(R)\eta T(R)A. \tag{8}$$

Now, combining equations 4, 6 and 8, the spatial average velocity is seen to be:

$$<v(t)> = \frac{M1}{M0} \tag{9}$$

that is, the spatial average velocity is simply equal to the first moment of the power spectrum of the received Doppler-shifted signal normalized by its zeroth moment.

This spatial average velocity is of value in its own right for purposes of evaluating flow in a vessel before and after an angioplasty procedure or other treatment. Alternatively, the spatial average velocity can be combined with an independent measurement of vessel cross-sectional area (based on fluoroscopy, for example) to provide a volumetric flow estimate.

Rather than utilizing a balloon dilatation catheter for the flexible elongate transducer carrying device, a guide wire 101 of the type shown in FIGS. 6-9 can be utilized. Such a guide wire is comprised of a flexible elongate element 102 which can be in the form of a hypo tube 102 having a suitable outside diameter as, for example, 0.016 inches, and having suitable wall thickness as, for example, 0.002 inches. In order to provide additional rigidity and torqueability for the guide wire 101, a core wire 103 formed of a suitable material such as stainless steel is provided. The core wire 103 can have a suitable diameter as, for example, 0.008 inches and extends through the hypo tube 102. Its distal extremity 104 is tapered for a distance of approximately 15 centimeters from a diameter of 0.008 inches to a diameter of 0.003 inches. The distal extremity 104 extends beyond the hypo tube 106 and extends into a coil spring 106 which is secured to the hypo tube 102 in an appropriate manner such as by soldering. The coil spring 106 is formed of two parts, a part 106a which is formed of stainless steel an the other part 106b of a more opaque material such as a palladium alloy or other material as described in U.S. Pat. No. 4,538,622. At the region where the two portions 106a and 106b are screwed together, the spring is bonded to the core wire 103 by solder or an epoxy 107. A safety wire or shaping ribbon 108 is provided. It is formed of a suitable material such as stainless steel ribbon and has a cross-sectional dimension of 0.001 inches×0.003 inches. The safety ribbon or shaping ribbon 108 extends from the solder or epoxy joint 107 to the distal extremity 109 of the coil spring 106. A transducer 111 of a suitable type as, for example, a piezoelectric crystal of the type hereinbefore described is carried by the distal extremity 109 of the coil spring 106 and is secured thereto by suitable means such as a tungsten-oxide loaded epoxy 112. As can be seen, the shaping wire 108 extends into the epoxy 112. Front and rear contacts 116 and 117 are provided on the transducer 111 and are connected to a two conductor wire 118 which extends rearwardly and interiorly of the spring 106 and extends into the hypo tube 102 between the core wire 103 and the interior of the hypo tube 102. The wire 118 extends out the distal extremity 119 of the hypo tube 102 and is connected to a male connector 121. The distal extremity of the hypo tube 119 can be secured to the core wire by suitable means such as an epoxy. The surface of the crystal serving as a transducer 111 can be coated with a suitable protective material such as a urethane coating 122. As shown, the spring 106 can extend for a predetermined distance, as for example, 1.5 centimeters beyond the tapered distal extremity 104. The portion 106b of the coil 106 can have a suitable length as, for example, 3 centimeters.

The guide wire 101 can have a suitable overall length, as for example, 175 centimeters. The crystal transducer 111 can have a suitable diameter as, for example 0.019 inches.

By providing a guide wire of this size, it is possible to utilize a guide wire in connection with conventional balloon dilatation catheters to perform angioplasty procedures.

Use and operation of the guide wire 101 in conjunction with the system and apparatus hereinbefore described is very similar to that described in conjunction with the use of the balloon dilatation catheter. After the guide wire and the balloon dilatation catheter have been advanced into a region adjacent to the stenosis, a volumetric flow measurement can be made by attaching the male connector 121 to the female connector 51 of the flow meter 13. A reading will be given on the digital display 56 giving an indication of the volumetric blood flow. After a dilatation procedure has been accomplished, the balloon dilatation catheter can be withdrawn proximal to the stenosis and a volumetric flow measurement can again be made by withdrawal of the guide wire to a position proximal to the stenosis and in approximately the same position it was in during flow measurement prior to dilation of the stenosis.

Typically for use with the guide wire carried transducer, the transducer would have a suitable frequency as, for example, 10 MHz and a diameter of 0.5 millimeters to produce a beam divergence of approximately 20° which will again produce a far field uniform beam capable of insonifying a 2.5 millimeter vessel at a range gate depth of 10 millimeters. Thus again, it can be seen that this makes possible instantaneous volumetric flow measurements before and after an angioplasty procedure.

In FIGS. 10 and 11 another embodiment of the flexible elongate transducer carrying device is shown in the form of a guide wire 131. The guide wire 131 consists of a flexible elongate element 132 which serves as the main shaft for the guide wire 131. The element 132 is formed of a suitable material such as a stainless steel tubing often called a hypo tube. This tube as hereinafter described performs a number of functions. It serves as a torsional member, as a conductor and also as a conduit for carrying other conductors internally. The hypo tube has a suitable outside diameter as for example 0.0165 inches and a suitable wall thickness, as for example, 0.002 inches to provide an inside diameter of 0.0125 inches. The element 132 can have a suitable length, as for example, 150 to 175 centimeters.

A core wire 133 is disposed within the flexible elongate element 132 and is also formed of a suitable material such as stainless steel and provides additional stiffness for the main shaft of the guide wire 131. The core wire 133 can be solid and has an outside diameter ranging from 0.0065 to 0.0085 inches and has a length which sets so that it extends beyond the distal extremity 134 of the flexible elongate element 132. The forwardmost extremity of the core wire 136 is provided with tapered portions 136a and 136b. Portion 136a has a length of approximately 4 centimeters and which tapers down from the exterior dimension of the core wire to a dimension of 0.005 inches.

The portion 136b has a length of approximately ½ centimeter and tapers down from 0.005 inches to 0.002 inches.

An insulating sleeve 141 is formed of a suitable insulating material such as a polyimide tubing. The polyamide tubing forming the sleeve 141 forms a relatively tight fit with the exterior surface of the core wire 136 and fits within the hypo type serving as the flexible elongate element 132. The sleeve 141 serves to insulate the stainless steel core wire 136 from the hypo tube serving as a flexible elongate element 132 so that they can serve as separate and independent electrical conductors.

The insulating sleeve 141 is formed of two portions 141a and 141b. The portion 141a extends to near the distal extremity 134 of the flexible elongate element or tubing 132. The other portion 141b extends over the forward extremity of the core wire 136 and in particular over the tapered portion 136a and has its proximal extremity seated within the flexible tubing 132 so that it abuts the portion 141a. The portion 141b can be formed of the same material as portion 141a and can have the same wall thicknesses and radial dimensions.

Flexible coil means 146 is secured to the distal extremity 134 of the flexible tubing 132 and consists of a coil 147 formed of a suitable material such as stainless steel with the coil being formed of stainless steel wire having a diameter of 0.002–0.003 inches and a coil 148 which is formed of a material which is more radiopaque than stainless steel, as for example, a palladium alloy also formed of wire having a diameter of 0.002–0.003 inches.

A cylindrical crystal 151 which serves as a Doppler transducer is mounted on the distal extremity of the coil 148. Means is provided for establishing electrical contact with the crystal 151 and consists of an insulated conductor 152 which is connected to the front or distal face of the crystal 151 and extends rearwardly within the interiors of the coils 148 and 147 where it is connected to the distal extremity 134 of the flexible tubing 132. This conductor 152 is provided because it has been found that the resistance provided by the stainless steel coil 147 and the paladium alloy coil 148 is greater than desired. Conductor means is also provided for establishing electrical contact with the rear side of the crystal 151 and consists of a conductive braid 153 which is formed of three stands 156, 157, and 158 of an insulated beryllium copper wire, the wire itself having a diameter of 0.001 inches. Braiding of the wire is used rather than twisting of the wire because this gives a greater flexibility to the wires while retaining a very high tensile strength. For example, the beryllium copper wire has a tensile strength approximately twice that of pure copper wire. The conductive braid 153 is secured to the rear side of the crystal 151 by a conductive adhesive joint 161 of a conventional type. As shown in FIG. 11, the braid extends around the distal extremity of the core wire 136 and is secured to the core wire 136 intermediate the ends of the tapered portion 136a by a conductive adhesive joint 162.

An additional adhesive joint 163 is provided between the proximal extremity of the coil 147 and the distal extremity of the flexible tubing 134 and the insulating sleeve 141. Another adhesive joint 164 is provided between the proximal extremity of the sleeve portion 141a and the distal extremity of the sleeve portion 141b and the exterior surface of the core wire 136. Similarly, an adhesive joint 166 is provided between the proximal extremity 133 of the flexible elongate member 132 and the proximal extremity of the insulating layer 141a. Similarly, an adhesive joint 167 is provided between the proximal extremity of the sleeve portion 141a and the exterior surface of the core wire 136. The adhesive joints 163, 164, 166 and 167 can be formed on any suitable conventional non-conductive adhesive. These adhesive joints ensure that torsional force applied to the outer flexible stainless steel tubing 132 is transferred to the insulating sleeve 141 and to the core wire 136 so that torsional forces applied to the guide wire are transferred to the distal extremity of the guide wire.

A flexible conductor cable 171 is connected to the proximal extremity of the guide wire and carries conductors 172 and 173 within insulating material 174. Conductor 172 is secured to the proximal extremity of the flexible tubing 132 whereas conductor 173 is secured to the proximal extremity of the core wire 136. The cable 171 is terminated in a connector 176.

A lens 181 is mounted on the front surface of the crystal 151. The lens can be formed of a suitable material such as thermosetting No. PC12 epoxy supplied by Dexter Hysol, 10501 East Don Julien Road, City of Industry, Calif. 91746. The lens is molded or machined to be approximately hemispherical in shape, and is secured to the crystal 151 by a conventional adhesive which provides excellent acoustical properties. Alternatively, the lens can be formed via surface tension so that it takes a natural hemispherical shape. This is due to the natural forces exerted on the droplet of adhesive which forms the lens. The force exerted causes the viscous material to assume a hemispherical shape, exactly in the way that a droplet of water beads upon a newly waxed automobile. Formation in this manner provides an excellent exterior high quality lens surface finish which facilitates the formation of a beam pattern without substantial scattering of ultrasonic energy. This hemispherical lens creates a very uniform diverging beam which extends over approximately 90° thereby providing a uniform insonification across the vessel being examined.

The connector 176 can be connected to a flow meter of the type hereinbefore described to provide an indication of flow being measured by the Doppler crystal 151.

With a guide wire of the type shown in FIGS. 10 and 11, it is possible for the physician performing a coronary angioplasty procedure to insert the guide wire of the present invention in place of the guide wire utilized in the angioplasty and dilatation catheter to make a blood flow measurement prior to the dilatation of the occlusion and immediately after the dilatation of the occlusion to ascertain the improvement in blood flow. The guidewire-type construction for the flow measurement device facilitates making of pre and post stenosis flow measurements.

It is also possible to utilize the present guide wire to introduce the angioplasty dilatation catheter even though this is not a recommended procedure. This can be accomplished by loading of the guide wire into the angioplasty dilatation catheter and then introducing the guide wire followed by the dilatation catheter into the vessel of the patient.

It has been found that the guide wire shown in FIGS. 10 and 11 has excellent mechanical properties. The concentricity or coaxial construction provided in the guide wire gives a high degree of torqueability and steerability to the device. The construction of the tip of the guide wire makes it very floppy so that it can be readily steered into small vessels in the cardiovascular system. The conductive braid in addition to serving as a conductor provides a safety wire to prevent the tip of the guide wire from becoming separated from the main shaft of the guide wire. The beryllium copper conductive braid has high tensile strength while still giving high flexibility to the tip of the guide wire. It also gives good conductivity with a high resilience.

Still another embodiment of a guide wire incorporating the present invention is shown in FIG. 12 which is particularly useful in the event significant electrical noise problems are encountered which require shielding of the conductors utilized in the guide wire.

The guide wire 191 shown in FIG. 12 is constructed in a manner quite similar to that shown in FIGS. 10 and 11. Thus it is provided with stainless steel tubing 132, a core wire 136 and coil means 146. It is also provided with a Doppler crystal 151 and a lens 181. In order to achieve a shielding to isolate the conductors connected to the crystal 151 from electrical noise, a third electrical conductor 192 is provided which is in the form of a flat wire helically wound around the core wire 136. This third electrical conductor 192 can be an insulated wire which is wrapped around the core wire 136 or alternatively it can be embedded in an insulating material 193 as shown in FIG. 12 so that it is insulated from the core wire 136 and also insulated from the flexible tubing 132. A conductor 152 is connected to the helical wrapped conductor 192. The conductor 152 can be connected to the front side of the crystal 151 as described in connection with the embodiment shown in FIGS. 10 and 11 whereas the rear side of the crystal 151 is connected by the conductive braid 153 to the core wire 136 in the manner hereinbefore described. With this being the case, the outer stainless steel tubing 132 can serve as a grounded shield for shielding the conductors 192 and the core wire 136 from external electrical signals and thereby prevent distortion of the signal received from the crystal 151 from extraneous sources. Thus it would only be necessary that the cable 171 be provided with three conductors rather than two conductors shown in FIGS. 10 and 11.

It can be seen that the guide wire shown in FIG. 12 can be utilized in the same manner as described in the previous embodiments. Although it typically is not utilized for introducing a dilatation catheter into the coronary vessel once the dilatation catheter is in place and the guide wire serving as the flow probe is in place, it may be used to advanced the dilatation catheter from one stenosis to the next. It is for that reason that the torsional capabilities of the guide wire are important because it facilitates using it as a steerable guide wire and to advance the dilatation catheter from one stenosis to the next. It is also important that the guide wire have a relatively flexible tip so that it will not cause trauma in the vessel in which it is advanced.

Still another embodiment of the guide wire incorporating the present invention is shown in FIG. 13 in which the flexible tubing 132 or the core wire 136 are not utilized as conductors. In this embodiment the guide wire 194 includes an additional conductor 196 is provided which is connected to the rear side of the Doppler crystal 151. This wire 196 with the wire 152 which is connected to the front side of the crystal 151 are connected to a flat conductive cable comprising multiple wires in the form of two wires 196 and 197 which are connected respectively to the conductors 152 and 196. This relatively flat multi-conductor cable 196 is wrapped in a helical fashion around the core wire 136 and is connected to the cable 171. The adhesive joints 163 and 166 are utilized to establish torsional transmitting capabilities between the tubing 132 and the conductor cable 196 as well as to the core wire 136. In this embodiment, the braid 153 is made of stainless steel wire and merely serves as a safety wire and does not serve as a conductor. Thus in this embodiment it can be seen that the stainless steel tubing 132 can also serve as a shield to keep out extraneous electrical signals from the conductors 197 and 198 to ensure that a noise free signal is received from the Doppler crystal 151.

Another embodiment of the guide wire incorporating the present invention is shown in FIG. 14. The guide wire 201 shown in FIG. 14 includes a flexible elongate member 202 in the form of stainless steel hypodermic tubing. The member or tubing 202 is provided with a distal extremity 203. The tubing 202 has a cylindrical passage 204 extending therethrough and has a core wire 206 disposed therein. The core wire 206 has a diameter slightly less than the interior diameter of the passage 204 and does not extend through the length of the tubing 202. As shown particularly in FIG. 14, the core wire 206 terminates shortly after the distal extremity of the tubing 202 and is secured therein by suitable means such as a solder joint 207. The core wire 206 is provided with a shaft portion 206a which has a substantially continuous diameter ranging from 0.006 to 0.009 inches and preferably approximately 0.008 inches. The shaft portion 206a has a length of approximately 27 centimeters. The core wire is also provided with a tapered portion 206b which is tapered form 0.008 inches to 0.005 inches and has a length of approximately 2 centimeters. The core wire is provided with an additional tapered portion 206c which is tapered from 0.005 inches to 0.002 inches and has a length ranging from 1 to 2 centimeters. The core wire 206 is also provided with a cylindrical end portion 206d which has a diameter of 0.002 inches and has a suitable length such as 5 millimeters.

Coil means 208 of the type hereinbefore described is provided which is secured to the distal extremity of the flexible elongate member formed by the tubing 202. The coil means consists of a length of stainless steel coil 209 and a length of palladium alloy coil 211 with the stainless steel coil 209 being secured to the core wire 206 and to the distal extremity of the tubing 202 by a solder joint 207. A Doppler crystal 212 is secured to the distal extremity of the palladium alloy coil 211 by a solder joint 213. Two conductors 216 and 217 are secured to the front and rear sides of the Doppler crystal 212 and extend through the passage 204 and beyond the proximal extremity of the tubing 202 by extending through the coil means 208 and between the interior of the tubing 202 and the outside diameter of the core wire 206. A flexible braid 221 is provided which is embedded in the solder joint 213 and extends proximally from the distal extremity of the coil means 208 and over the distal extremity of the core wire 206 to the region where the coils 209 and 211 abut and into a solder joint 222 which bonds the abutting regions of the coils 209 and 211 and the proximal extremity of the braid 221. The flexible braid 221 differs from the braid hereinbefore described in that it need not be a good conductor. Thus, stainless steel can be utilized for such a braid. A lens 226 is mounted on the Doppler crystal 212 and serves the same purpose as the lens 181 hereinbefore described.

In this embodiment of the invention, the conductors 216 and 217 provide the connections to the crystal making it unnecessary for either the tubing 202 or the core wire 206 to serve as conductors.

The guide wire shown in FIG. 14 has a number of advantages. It has greater flexibility at its distal extremity, while providing the desired degree of stiffness in the area adjacent to the distal extremity and permitting the guide wire to follow tortuosities in the vessels. It has good torsion capabilities facilitating its steering in the vessels. Also the construction shown makes possible the use of a larger core wire and conductor wires which do not need to be flattened.

It has been found that the torsional and flexure properties of the guide wires of the present invention are virtually equal to that of existing guide wires utilized in angioplasty at the present time. In addition, however, the guide wires of the present invention provide the desired electrical properties for supplying signal to and from the Doppler crystal. In addition, the acoustical properties that are provided by the lenses 181 and 226, provide in the guide wire a combination of torsion flexure, electrical and acoustical properties which provide a flow probe that performs admirably under many applications and in particular, cardiovascular applications involving angioplasty. The guide wires of the present invention have the floppiness or flexure capabilities of conventional guide wires while still providing means for carrying the electrical signals to and from the Doppler crystal. The coaxial design utilized in the guide wires shown in FIGS. 10-14 provides excellent torsional capabilities. In addition, the construction makes it possible to maximize the size of the stainless steel core wire. The guide wire construction also makes it possible to provide maximum electrical noise rejection while still retaining the desired flexure and torsional capabilities for the guide wire.

Still another embodiment of a guide wire incorporating the present invention is shown in FIGS. 15, 16 and 17. The guide wire 231 shown in FIG. 15 consists of a flexible elongate member 232 in the form of stainless steel hypodermic tubing having a suitable outside diameter, as for example, 0.018 inches and having a wall thickness ranging from 0.0023 to 0.003 inches and preferably a wall thickness of 0.0026 inches. The member or hypodermic tubing 232 can have a suitable length such as 100 to 150 centimeters. The tubing 232 is provided with a centrally disposed passage 233 extending therethrough. It is also provided with a distal extremity 234 and a proximal extremity 236. A core wire 238 of suitable material such as stainless steel is provided and has a proximal extremity 239 which is disposed within the distal extremity 234 of the hypodermic tubing 232. The core wire can have the same diameter and length as the core wire 206 provided in the embodiment shown in FIG. 14. It is provided with a tapered distal extremity 241 in the same manner as with the guide wire 206.

Coil means 246 of the type hereinbefore described is secured to the distal extremity 234 of the hypodermic tubing 232 and consists of a length of a stainless steel coil 247 and a length of a palladium alloy coil 248.

A Doppler transducer or crystal 251 is secured to the distal extremity of the palladium alloy coil 248 by suitable means such as an adhesive joint 252. A pair of electrical leads 253 and 254 are provided in which the lead 253 is connected to the front surface of the crystal 251 and the lead 254 is connected to the rear surface of the crystal 251. The leads 253 and 254 can be formed of a suitable material such as 45 gauge copper wire which is provided with a covering of high temperature insulation of a conventional type which can withstand the temperature of melted solder. Thus, as shown each of the leads is provided with a conductor 256 which is circular in cross-section with an insulating covering 257 surrounding the same.

As can be seen, particularly from FIGS. 16 and 17, the leads 253 and 254 extend rearwardly from the crystal 251 interiorally of the coil means 246. A flexible braid 261 of stainless steel of the type hereinbefore described is provided within the coil 248 and ex tends rearwardly from the adhesive joint 252 and over the distal extremity 241 of the core wire 238. The flexible braid has its proximal extremity bonded to the distal extremity of the core wire 238 and to the coil means 246 by a solder joint 262. The solder joint 262, in addition, bonds together the abutting ends of the coils 247 and 248. An additional solder joint 264 is provided for bonding the proximal extremity of the stainless steel coil 247 to the distal extremity 234 of the hypodermic tubing 232 and also to form a bond with the proximal extremity of the core wire 238. A hemispherical lens 266 formed in the manner hereinbefore described is provided on the front surface of the Doppler crystal 251.

In connection with the embodiment of the guide wire shown in FIGS. 15, 16 and 17, special precautions are taken to ensure that the guide wire is not susceptible to attack from the fluid in which it is disposed, as for example, in blood or other saline solution. To this end, during the manufacture of the guide wire 231 and at the time that the electrical leads 253 and 254 are secured to the front and back sides of the crystal 251, a protective cover in the form of a conformal coating 268 is applied to the crystal. Such a conformal coating is typically deposited in a vacuum onto the crystal and is relatively thin, as for example, 0.0001 of an inch. Such a conformal coating can be provided on the Doppler crystal or transducer 251 and the leads attached thereto to a distance extending approximately at least two millimeters from the crystal. One material found to be satisfactory for such a protective conformal coating is Parylene, a polymeric coating, manufactured by Union Carbide.

The leads 253 and 254 are inserted through the palladium alloy coil 248 and the flexible braid is inserted into the palladium alloy coil 248. A protective tube 271 formed of a suitable material such as a polyimide is inserted into the stainless steel coil 247. The protective tube can have a suitable diameter such as 0.0100 inches ID with an OD of 0.0115 inches. The core wire 238 is then inserted into the coils 247 and 248. The distal extremities of the palladium alloy coil 248 and of the flexible braid 261 are secured to the Doppler crystal 251 by an adhesive joint 252 formed by an ultraviolet cured adhesive. Thereafter, the solder joints 262 and 264 can be applied. The insulation on the electrical leads 253 and 254 can withstand the temperature of the melted solder. Thereafter, the entire distal extremity of the guide wire 231, after it has been assembled, is coated with a second conformal coating 272 of Parylene to provide additional protection against attack by blood and other saline solutions. Parylene has been found to be a very suitable material for use in guide wires of the present construction because it permits elongations of over 200% without affecting the integrity of the coating. By utilizing such as conformal coating, it is possible to retain the desired characteristics of the guide wire without deleteriously affecting the desired characteristics to any significant extent. Thus with a Parylene conformal coating, the springiness of the tip can be retained. A Teflon coating 274 is provided on the exterior surface of the hypodermic tubing to reduce the friction between the guide wire 231 and the catheter into which it is introduced.

The guide wire 231 shown in FIG. 15 is provided with a micro-miniature connector 276 of the type which is described in copending application Ser. No. 265,909, filed Nov. 2, 1988. The details of this micro-miniature connector 276 therefore will not be described in this application. However, in general it consists of a first conductor 277 formed of a crimped core wire and a second conductor formed by a conductive sleeve 278. One of the electrical leads 253 and 254 is connected to the first conductor 277 and the other of the electrical leads 253 and 254 is connected to the second conductor 278. As can be seen, the micro-miniature connector 276 is mounted in the proximal extremity 236 of the hypodermic tubing 232.

The guide wire construction hereinbefore described in FIGS. 15, 16 and 17 has numerous advantages. The hypodermic tubing 232 serves as a flexible shaft. In addition, it provides a conduit for the electrical leads 253 and 254. It also provides a high degree of torque transmission while remaining as flexible as a solid stainless steel wire so that the guide wire 231 can be readily positioned in angioplasty procedures. The flexible braid 261 prevents longitudinal extension of the tip of the guide wire or, in other words, elongation of the palladium alloy coil 248 to prevent separation of the Doppler crystal or transducer from the guide wire. The flexible braid 261 formed of stainless steel maximizes tensile strength, while still permitting a high degree of flexibility in the tip of the guide wire. The use of a tapered core wire provides a smooth transition from the highly flexible tip of the guide wire to the less flexible hypodermic tube shaft. The two solder joints 262 and 264, in addition, to performing their mechanical connecting functions also increase the torque transmission of the guide wire. The use of the palladium alloy provides high radiopacity for the tip of the guide wire. Coating of the stainless steel hypodermic tubing 232 with the Teflon friction-reducing coating reduces the friction between the guide wire and the catheter in which it is used.

The spherical lens 266 which is formed by a surface tension provides a lens of natural shape which gives a wide dispersion of the ultrasound beam as, for example, an angle of 90° to obtain excellent coverage within the vessel in which the guide wire is disposed.

The micro-miniature connector 276 makes it possible to utilize the guide wire as a standard guide wire in exchanging catheters in a PCTA procedure. As hereinbefore explained, in order to protect the electrical leads 253 and 254 from the affects of blood or other substances which the guide wire may encounter a plurality of protective coatings is provided. The sheath or tube 271 formed of polyimide covers the electrical leads between the two solder joints 262 and 264 and thus protects the leads from coming in contact with blood which could seriously degrade the conductive qualities of the leads. The polymide sheath also provides mechanical insulation in that it prevents the electrical leads from chafing against and short circuiting to the stainless steel coil. In addition, the polyimide sheath 271 provides a slight amount of a desired stiffness to the guide wire in this region of the guide wire. Also, as pointed out previously, the Doppler transducer or crystal with the electrical leads attached thereto is coated with a conformal coating of Parylene which provides a durable barrier to protect the transducer and the connecting electrical leads from blood. In addition another conformal coating of Parylene is provided after completion of assembly of the guide wire by coating the entire distal extremity approximately the last 30 centimeters. This sheath 271 and the coating 268 and 272 protect the entire assembly from attack by blood and preserves the integrity of both the electrical and mechanical characteristics of the guide wire for indefinite periods of time and certainly for periods of time more than adequate to perform any conventional procedure, as for example, an angioplasty procedure in which such a guide wire is used.

From the foregoing it can be seen that a guide wire construction has been provided in which the portions of the electrical leads which could come in contact with blood, as for example, the portions of the leads extending through the coils are protected by the polyimide tube or sheath and the conformal coatings.

Another embodiment of the guide wire incorporating the present invention utilizing screw joints is shown in FIGS. 18 through 21 and is of a type which incorporates screw joints. The guide wire 281 shown in FIG. 18 consists of a flexible elongate member 282 in the form of stainless steel hypodermic tubing of the same dimensions described in conjunction with the guide wires shown in FIG. 15. The elongate member 282 is provided with a passage 283 extending therethrough. The elongate member 282 is provided with a distal extremity 284. A helical slot 286 is cut into the exterior surface of the distal extremity 284 and extends through the wall of the hypodermic tubing 282 to form threads. The helical slots 286 can be formed in a suitable manner such as by machining. Such a density would provide threads with a helix angle of 9.50° and a pitch of 0.00926 inches. Such helical slots can be formed by utilizing a diamond dicing saw with a very thin blade having a thickness ranging from 0.0015 to 0.0010 inches and by utilizing a helical drive mechanism to feed the distal extremity 284 into the diamond dicing saw.

Typically, the hypodermic tubing forming the elongate member 282 has an outside diameter ranging from 0.017 to 0.0178 inches and is coated with a suitable lubricant such as Teflon to facilitate movement of the guide wire 281 in a vessel of a patient. The inside diameter of the hypodermic tubing can vary from 0.014 to 0.015 inches to provide a wall thickness ranging from 0.0015 inches to 0.0025 inches. The helical slot or groove 286 has a width which can range from 0.0025 to 0.0045 inches. The threads formed by slot or groove 286 have a density which can range from 75 to 150 per inch and preferably about 108 per inch for tubing having a diameter of 0.018 inches or less.

An insulating and protective tube 287 formed of a suitable material such as polyimide is disposed in the passage 283 of the hypodermic tubing 282 and extends beyond the distal extremity 284 of the hypodermic tubing. A coil 288 formed of a suitable material such as stainless steel is threaded into the helical slots or grooves 286 and extends over the portion of the insulating tube 287 extending beyond the distal extremity 284 of the elongate member 282. This connection serves to form a screw joint 289 rather than the solder joint hereinbefore described. To provide high x-ray visibility, a palladium coil 291 is threaded into the stainless steel coil 288 as shown in FIG. 2 and solder 292 is applied to provide a solder screw joint 293 between the stainless steel coil 288 and the palladium coil 291.

A screw tip 296 is provided and can be formed of a suitable material such as stainless steel and have the same dimensions as the hypodermic tubing forming the elongate member 282. The tip can have a suitable length such as 0.050 to 0.060 inches. A helical thread or recess 297 is formed in the exterior surface of the tip 296 and receives the distal extremity of the palladium coil 291. The helical recess 297 is formed in a manner similar to the helical slots 286. However, rather than being cut all the way through as with the helical slots 286, the helical recess 297 extends only through a portion of the wall forming the tip 296. Thus, with the wall thickness of 0.004 to 0.005, the recess or thread can have a depth ranging from 0.0025 to 0.0038 inches and can be squared or have a full radius.

When the tip 296 is threaded into the distal extremity of the coil 291, the tip itself is aligned with respect to the coil 291. The tip 296 is provided with a cylindrical recess 301 at its distal extremity which opens in a forward direction. The recess 301 can have a depth ranging from 0.015 to 0.020 inches and can have a diameter ranging from 0.0155 to 0.0166 inches. A Doppler transducer 302 and a lens 303 are disposed within the recess 301 and are adhered therein by suitable means such as an adhesive 304 disposed between the side wall of the recess 301 and the transducer 302 so that the rear of the transducer is free or in air.

A core wire 306 formed of a suitable material such as stainless steel extends through the insulating and protective tube 287 and is provided with a tapered distal extremity 307 which adjoins a shaping ribbon 308 having a rectangular configuration and which is secured to the screw tip 296 by suitable means such as solder 309. The screw tip 96 in addition to being threaded into the coil 291 also has the coil soldered to the tip. Conductive leads 311 and 312 are provided which extend within the insulating and protective tube 286 and over the core wire 306. They are connected to the front and back sides of the transducer 302 as shown particularly in FIG. 18.

The entire coil assembly or means comprised of the coils 288 and 291 and the screw joint 293 and the screw tip 296 is Parylene coated in the manner hereinbefore described for the previous embodiments.

Operation and use of the guide wire 281 is the same as hereinbefore described with the previous embodiments. The advantage of the present embodiment is that the transducer 302 and the lens 303 are incorporated in an assembly which is very difficult to separate from the remainder of the guide wire. This is accomplished by placing the transducer 302 and the lens in the cup-shaped recess 301 provided at the tip of the guide wire. Tip separation is also prevented by the use of the soldered screw tip 296 configuration which is utilized for securing the tip 296 to the coil 291. An excellent mechanical joint is provided for securing the tip 296 to the coil 291. The recessing of the transducer 302 which is in the form of a Doppler crystal holds the same in place so there is no chance of the transducer 302 and the lens 303 being separated from the tip 296.

The screw joints provided in the guide wire 281 in addition to providing better mechanical connections also provides the advantage of providing strain relief transitions from the relatively stiff hypo tube forming the elongate member 282 to the flexible coil 288 used at the tip and also a similar transition between the coil 291 and the tip 296. Therefore the construction of the present embodiment provides very strong joints which have excellent tensile and bending load characteristics.

It should be appreciated that the cup-shaped recess 301 which is provided can be utilized for accommodating various types of transducers other than the Doppler crystal hereinbefore described. For example, it can be utilized for housing various types of sensors as, for example, a pressure transducer.

The same principles which have been utilized in the distal extremity of the guide wire 281 can also be utilized in the proximal extremity in which helical slots 316 are provided in the proximal extremity of the hypodermic tubing forming the flexible elongate member 282. A coil spring 317 formed of a suitable material such as stainless steel is threaded into the slots 316 as shown in FIG. 18. The insulating sleeve 287 extends beyond the coil spring 317. A connector 321 is mounted in the spring 317 and extends into the proximal extremity of the hypodermic tubing 282 and is secured therein by suitable means such as an adhesive. The connector 321 is formed of a suitable conducting material such as stainless steel. It serves the same purpose as the connector 276 shown in FIG. 15. The FIG. 18, the proximal extremity of the connector 321 is not crimped. It can be provided with a crimp is desired of the type shown in FIG. 15. If not desired, a non-crimped cylindrical connector 321 can be provided as shown in FIG. 18.

Figures 20, 21:
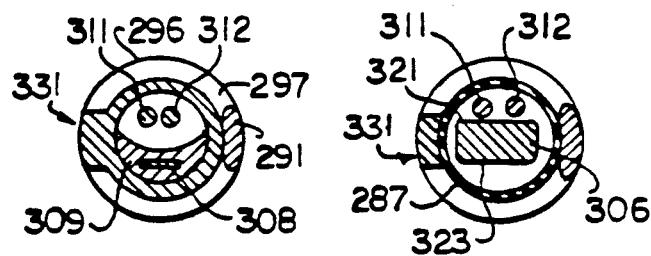
FIG. 20 is a cross sectional view taken along the line 20—20 of FIG. 18.
FIG. 21 is a cross sectional view taken along the line 20—13 of FIG 18.

In order to accommodate the conducting wires 311 and 312, the portion of the connector 321 disposed within the proximal extremity of the hypodermic tubing 282 is provided with flats 322 and 323 as shown in FIG. 21.

The construction shown for the proximal extremity of the guide wire 282 has the same advantages as the construction provided on the distal extremity of the guide wire. A good mechanical connection is provided between the hypodermic tubing 282 and the coil spring 317 and the connector 321. The coil spring also provides a strain relief transition from the hypodermic tubing 282 to the connector 321.

One of the principal advantages of mounting the transducer 302 within the cup-shaped recess 301 is that the adhesive 304 is provided on the circumference of the transducer 302 but is not provided to the rear of the transducer so that the rear or back side of the transducer 302 is exposed to air and can readily flex. This enhances the Doppler capabilities of the crystal or transducer.

It should be appreciated that with these screw type joints provided in the guide wire 281, the springs are threaded into the helices of the guide wire to provide an integrated construction. However, it should be appreciated that a non-integral construction could be provided by bonding the coil to the hypodermic tubing without threading the coil into the helices. It is believed that this is not as desirable because not as good a mechanical connection is provided. However, such a construction would provide a gradual transition in stiffness form the hypoderic tubing to the coil spring.

Figure 22:
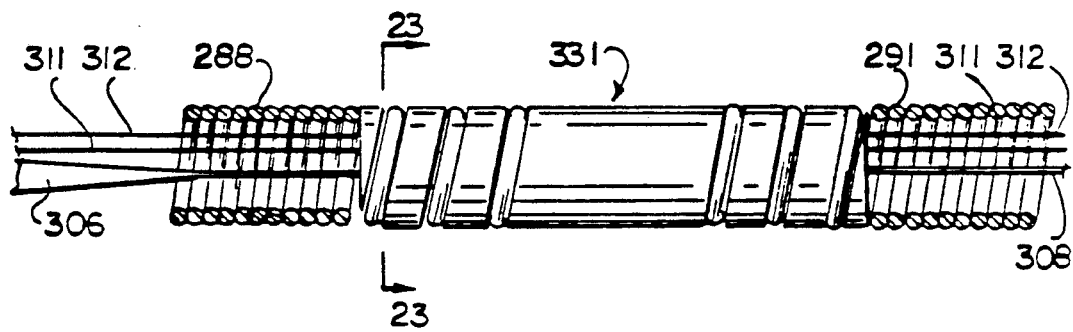
FIG. 22 is a view of a portion of a guide wire incorporating the present invention which is partially in cross section showing the use of an intermediate screw joint.
Figure 23:
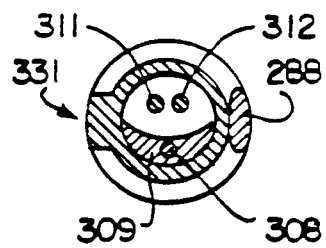
FIG. 23 is a cross sectional view taken along the line 23—23 of FIG. 22.
Figure 24:
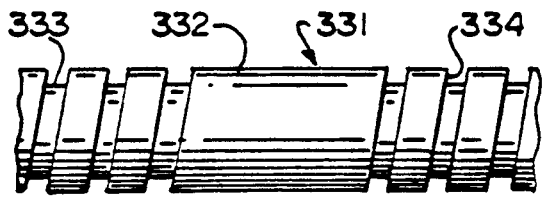
FIG. 24 is an elevational view of an intermediate screw joint used in the guide wire shown in FIGS. 22 and 23.

Another embodiment of a screw joint connection which can be utilized in the guide wire 281 is shown in FIGS. 22-24. As shown therein, rather than two coils 288 and 291 being threaded together as disclosed in FIG. 18, they are interconnected by an intermediate screw joint 331. The intermediate screw joint 331 is formed of a length of hypodermic tubing 332 of the same type utilized for the elongate member 282 and is provided with helical recesses 333 and 334 at opposite ends which are formed in the same manner as the helical recesses 297 in the tip 296. As shown in FIG. 22, the screw joint 331 is utilized for interconnecting the two coils 288 and 291 by threading the coil 288 into the helical recesses 333 and threading the coil 291 into the helical recesses 334. The conductors 311 and 312 and the shaping ribbon 308 extend through the screw joint 331 in the manner shown. From this construction, it can be seen that a strong mechanical connection with good alignment has been provided between the two coils 288 and 291. The entire assembly which is shown in FIG. 22 can be Parylene coated in the manner hereinbefore described.

It is apparent from the foregoing that there has been provided a system, apparatus and method for measuring volumetric flow of blood in a vessel. This can be accomplished by the use of a single transducer positioned intravascularly to produce a beam of uniform insonification which encompasses the entirety of the blood vessel. By utilizing a calculated correctional factor applied to the signal obtained from a first moment detector, accurate measurement of volumetric blood flow may be obtained. These blood flow readings are obtained with little or no signal interference from vessels beyond the boundaries of the wall of the vessel in which the transducer is located. The extremely small transducers which are utilized make it possible to produce a far field uniform beam which encompasses the entirety of the vessel lumen. Volumetric flow measurements obtained using this uniform beam are substantially independent of the angle and orientation of the transducer in the vessel and of the flow profile within the blood vessel.

It should be appreciated that although the present invention has been described particularly for use in the measuring of the flow of blood in a vessel, the present invention also can be utilized for measuring other liquids in other types of conduits if desired.

What is claimed is:

1. In a joint construction for a medical guide wire joining a tubular member to a helical coil having an elongate element extending therethrough, the tubular member having an outside diameter no greater than the outside diameter of the coil and having a wall defining a passage extending therethrough and having an exterior surface, the tubular member having an end portion with a helical recess formed therein extending through said outer surface to form a helical thread, said helical coil having a passage extending therethrough and having an end portion threaded into the helical recess to fixedly secure the coil to the tubular member so that the passage in the tubular member and the passage in the coil are in alignment.

2. A construction as in claim 1 wherein the tubular member has another end portion with a helical recess therein extending through the outer surface of the wall to form another helical thread together with another helical coil having a passage extending therethrough and having an end portion threaded into said another helical thread of said another end portion of the tubular member to fixedly secure said another coil to said tubular member so that the passage in said another helical coil is in alignment with the passage in the tubular member.

3. A construction as in claim 1 wherein the threads have a density ranging from 75 to 150 threads per inch.

4. A construction as in claim 1 wherein the threads have a density of approximately 108 threads per inch.

5. A construction as in claim 1 wherein approximately 2.5 to 5.0 threads are provided.

6. A construction as in claim 1 wherein the threads only extend partially through the wall of the member.

7. A construction as in claim 1 wherein the threads are rectangular in cross section.

8. A construction as in claim 1 wherein the coil has an outer surface, and wherein the outer surface of the tubular member and of the coil are of the same size and with the helical recess being of a depth so that the outer surface of the coil spring is flush with the outer surface of the tubular member.

9. A construction as in claim 1 wherein said coil is in the form of a flexible spring.

10. A construction as in claim 1 wherein said coil and said another coil are in the form of flexible springs.

* * * * *

UNITED STATES PATENT AND TRADEMARK OFFICE
CERTIFICATE OF CORRECTION

PATENT NO. : 5,163,445

DATED : November 17, 1992

INVENTOR(S) : Jeffrey J. Christian, et al.

It is certified that error appears in the above-identified patent and that said Letters Patent is hereby corrected as shown below:

On the title page: Item [54]: Column 1, lines 1-5 should read:
In The Title: JOINT CONSTRUCTION FOR USE WITH APPARATUS, SYSTEM AND METHOD FOR MEASURING SPATIAL AVERAGE VELOCITY AND/OR VOLUMETRIC FLOW OF BLOOD IN A VESSEL [APPARATUS, SYSTEM AND METHOD FOR MEASURING SPATIAL AVERAGE VELOCITY AND/OR VOLUMETRIC FLOW OF BLOOD IN A VESSEL AND SCREW JOINT FOR USE THEREWITH.

Column 1, line 29: tensively in the literature, as for example, in Cole [in] et al.

Column 1, line 60: contained entirely within the blood vessel of interest and is Column 4, line 41: [20-13] 21-21 of FIG. 18

Column 6, line 30: provided with a power cord 53 which is adapted to be

Column 6, line 34: meter 13 is also provided with an analog output 57 which

UNITED STATES PATENT AND TRADEMARK OFFICE
CERTIFICATE OF CORRECTION

PATENT NO. : 5,163,445

DATED : November 17, 1992

INVENTOR(S) : Jeffrey J. Christian, et al.

It is certified that error appears in the above-identified patent and that said Letters Patent is hereby corrected as shown below:

Column 8, line 59: forms of the gate [12] 72 relates to the particular shape of the Column 9, lines 7-8: as determined by the frequency divider 62. The filter [73] 74 and [74] 75 may also include compensation for the "(sine Column 12, Equation 8: $M_\_ = 1(R)\_ \ T \ (R)\_$      (8)

Column 12, line 59: element [102] which can be in the form of a hypo tube 102

Column 13, line 2: distal extremity 104 extends beyond the hypo tube [106] 102

Column 13, line 6: part 106a which is formed of stainless steel [an] and the other Column 13, line 15: inches. The safety [ribbon] wire or shaping ribbon 108 extends

UNITED STATES PATENT AND TRADEMARK OFFICE
CERTIFICATE OF CORRECTION

PATENT NO. : 5,163,445

DATED : November 17, 1992

INVENTOR(S) : Jeffrey J. Christian, et al.

It is certified that error appears in the above-identified patent and that said Letters Patent is hereby corrected as shown below:

Column 13, lines 29-30: out the [distal] <u>proximal</u> extremity 119 of the hypo tube 102 and is connected to a male connector 121. The [distal] <u>proximal</u> extremity Column 14, line 21: A core wire [133] <u>136</u> is disposed within the flexible elon- Column 14, line 25: wire [133] <u>136</u> can be solid and has an outside diameter rang- Column 14, line 38: lating material such as a polyimide tubing, the poly[a]<u>i</u>m-

Column 14, line 41: and fits within the hypo [type] <u>tube</u> serving as the flexible Column 15, lines 30-31: tween the [proximal] <u>distal</u> extremity of the sleeve portion 141a and the [distal] <u>proximal</u> extremity of the sleeve portion 141b and Column 17, line 13: it may be used to advance[d] the dilatation catheter from

UNITED STATES PATENT AND TRADEMARK OFFICE
CERTIFICATE OF CORRECTION

PATENT NO. : 5,163,445
DATED : November 17, 1992
INVENTOR(S) : Jeffrey J. Christian, et al.

It is certified that error appears in the above-identified patent and that said Letters Patent is hereby corrected as shown below:

Column 17, lines 25-26:  wire 194 includes an additional conductor 196 [is provided] which is connected to the rear side of the Dop- Column 17, line 30:  ple wires in the form of two wires [196] 197 and [197] 198 which Column 17, line 32:  196.  This relatively flat multi-conductor cable cable [196] is Column 17, line 37:  tor cable [196] as well as to the core wire 136.  In this Column 20, line 29:  ing.  By utilizing such a[s] conformal coating, it is possible Column 22, line 67:  screw tip [96] 296 in addition to be threaded into the coil Column 23, line 2:  insulating and protective tube [286] 287 and over the core

UNITED STATES PATENT AND TRADEMARK OFFICE
CERTIFICATE OF CORRECTION

PATENT NO. : 5,163,445

DATED : November 17, 1992

INVENTOR(S) : Jeffrey J. Christian, et al

It is certified that error appears in the above-indentified patent and that said Letters Patent is hereby corrected as shown below:

Column 23, line 55: 276 shown in FIG. 15. [The] In FIG. 18, the proximal ex-

Signed and Sealed this

Twenty-first Day of June, 1994

BRUCE LEHMAN

Attest:

Attesting Officer

Commissioner of Patents and Trademarks